United States Patent
Super

(10) Patent No.: US 10,602,972 B2
(45) Date of Patent: Mar. 31, 2020

(54) METHOD OF MEASURING ATTENTION

(71) Applicants: UNIVERSITAT DE BARCELONA, Barcelona (ES); INSTITUCIÓ CATALANA DE RECERCA I ESTUDIS AVANÇATS, Barcelona (ES)

(72) Inventor: Hans Super, Canet de Mar (ES)

(73) Assignees: UNIVERSITAT DE BARCELONA, Barcelona (ES); INSTITUCIÓ CATALANA DE RECERCA I ESTUDIS AVANÇATS, Barcelona (ES)

(*) Notice: Subject to any disclaimer, the term of this patent is extended or adjusted under 35 U.S.C. 154(b) by 252 days.

(21) Appl. No.: 14/395,808

(22) PCT Filed: Dec. 21, 2012

(86) PCT No.: PCT/EP2012/076654
§ 371 (c)(1),
(2) Date: Oct. 20, 2014

(87) PCT Pub. No.: WO2013/159841
PCT Pub. Date: Oct. 31, 2013

(65) Prior Publication Data
US 2015/0112224 A1    Apr. 23, 2015

(30) Foreign Application Priority Data
Apr. 24, 2012  (EP) .................................... 12380018

(51) Int. Cl.
*A61B 5/16*    (2006.01)
*A61B 3/02*    (2006.01)
(Continued)

(52) U.S. Cl.
CPC ................ *A61B 5/168* (2013.01); *A61B 3/02* (2013.01); *A61B 3/113* (2013.01); *G08B 21/06* (2013.01)

(58) Field of Classification Search
CPC .................................. A61B 3/02; A61B 5/168
(Continued)

(56) References Cited

U.S. PATENT DOCUMENTS 6,091,334 A * 7/2000 Galiana .................. G08B 21/06
340/439
6,120,461 A * 9/2000 Smyth .................... A61B 3/113
600/558
(Continued)

FOREIGN PATENT DOCUMENTS

EP        0590231       4/1994
WO    WO 2008/129356    10/2008

OTHER PUBLICATIONS

Thiagarajan P, Ciuffreda KJ & Ludlam DP. Vergence dysfunction in mild traumatic brain injury (mTBI): a review. Ophthalmic Physiol Opt 2011, 31, 456-468. doi: 10.1111/j.1475-1313.2011.00831.x.*
(Continued)

*Primary Examiner* — Patrick Fernandes
(74) *Attorney, Agent, or Firm* — Squire Patton Boggs (US) LLP

(57) ABSTRACT

In a first aspect, the present invention provides a method of measuring attention of a person comprising presenting one or more stimulus aimed at attracting attention of the person; and obtaining positions of the eyes of the person. The method further comprises detecting one or more eye fixations from the obtained positions of the eyes; and measuring the angle of convergence of the eyes over time from the obtained positions of the eyes during one or more of the detected eye fixations.

19 Claims, 7 Drawing Sheets

(51) Int. Cl.
*A61B 3/113* (2006.01)
*G08B 21/06* (2006.01)

(58) Field of Classification Search
USPC .......................................................... 600/558
See application file for complete search history.

(56) References Cited

U.S. PATENT DOCUMENTS

| | | | | |
|---|---|---|---|---|
| 6,364,486 | B1* | 4/2002 | Ball | A61B 3/024 351/203 |
| 6,520,921 | B1* | 2/2003 | Patton | A61B 5/01 600/300 |
| 7,988,287 | B1* | 8/2011 | Butler | A61B 3/1015 351/210 |
| 2003/0028121 | A1* | 2/2003 | Blazey | A61B 5/01 600/549 |
| 2004/0105073 | A1* | 6/2004 | Maddalena | A61B 3/032 351/205 |
| 2005/0174536 | A1* | 8/2005 | Hanaki | A61B 3/0091 351/205 |
| 2006/0270945 | A1* | 11/2006 | Ghajar | A61B 3/113 600/558 |
| 2007/0291232 | A1 | 12/2007 | Marshall | |
| 2008/0212032 | A1* | 9/2008 | Seiller | G09B 19/0038 351/246 |
| 2010/0073469 | A1* | 3/2010 | Fateh | A61H 5/00 348/62 |
| 2010/0092929 | A1* | 4/2010 | Hallowell | G09B 7/00 434/167 |
| 2010/0201948 | A1* | 8/2010 | Sahraie | A61B 3/0091 351/239 |
| 2010/0280372 | A1* | 11/2010 | Poolman | A61B 5/04842 600/437 |
| 2011/0157550 | A1* | 6/2011 | Chen | A61B 3/145 351/206 |
| 2012/0105609 | A1* | 5/2012 | Qi | A61B 3/08 348/54 |
| 2012/0190968 | A1* | 7/2012 | Raber | A61B 5/16 600/411 |

OTHER PUBLICATIONS

Kapoula, Z. & Bucci, M.P. J Neurol (2007) 254: 1174. doi:10.1007/s00415-006-0460-0.*
Convergence and divergence exhibit different response characteristics to symmetric stimuli. Hung GK1, Zhu H, Ciuffreda KJ. Vision Res. May 1997;37(9):1197-205.*
The influence of subject instruction on horizontal and vertical vergence tracking. Stevenson SB1, Lott LA, Yang J. Vision Res. Oct. 1997;37(20):2891-8.*
Ebisawa et al., "Relation Between Attention and Characteristics of Saccade During Tracking Eye Movement", Systems & Computers in Japan, Wiley, Hoboken, NJ, US, vol. 19, No. 10, pp. 70-78 (1988).
Posner "Measuring Alertness", Annals of the New York Academy of Sciences, vol. 1129, No. 1, pp. 193-199 (2008).
Raz et al., "Typologies of attentional networks", Nature Reviews Neuroscience, vol. 7, No. 5, pp. 367-379 (2006).
Stevenson et al: "The influence of subject instruction on horizontal and vertical vergence tracking", Vision Research, Pergamon Press, Oxford, GB, vol. 37, No. 20, pp. 2891-2898 (1997).

* cited by examiner

METHOD OF MEASURING ATTENTION

The present invention relates to a method of measuring attention of a person and to a computer program product and a system suitable for carrying out such a method.

BACKGROUND ART

Most of the sensory information that reaches the human brain does so through the eyes. When a person looks, he/she scans the visual environment with saccadic eye movements. He/she shifts gaze 2-3 times per second. Between two consecutive saccades the eyes hold still for a brief period, typically between 100 and 1000 ms. During this period of stable gaze (or eye fixation), visual information at the fovea is processed in more detail. The fovea is a small centre area of the human retina and has a very high visual acuity. It covers a few degrees of visual angle. So to get a clear view of the world, the brain must turn the eyes so that the image of the object of regard falls on the fovea. Eye movements are thus very important for visual perception. For that reason, eye fixations (duration, location, frequency, repetition, etc.) are considered to tell how important and attended regions are for the subject.

During an eye fixation, objects in the person's periphery disappear from the person's perception (Troxler effect). To prevent this, small eye movements during fixation are produced. Several studies demonstrate that micro-saccades during fixation may be ones that prevent perception during fixation [Martinez-Conde, S., Macknick, S. L., Troncoso, X. G., & Hubel, D. H. (2009). *Microsaccades: a neurophysiological analysis. Trends in Neurosciences,* 32, 463-75]. However, other studies provide arguments showing that fixational micro-saccades may be laboratory artefacts and may have no role in visual functioning [Collewijn, H., & Kowler, E. (2008). *The significance of microsaccades for vision and oculomotor control. Journal of Vision,* 8(14), 20, 1-21]. Thus the role of micro-saccades in visual perception is still debated. Besides perception, it is debated whether micro-saccades have a role in visual attention. On the one hand, micro-saccade direction may be a reliable on-line measure of attention [Engbert, R., & Kliegl, R. (2003). *Microsaccades uncover the orientation of covert attention. Vision Research,* 43, 1035-45]. On the other hand, fixational eye movements may not be an index of covert attention [Horowitz, T. S., Fine, E. M., Fencsik, D. E., Yurgenson, S. and Wolfe, J. M. (2007). *Fixational eye movements are not an index of covert attention. Psychological Science,* 18, 356].

The eyes receive a slightly different projection of the image because of the two eyes' different positions on the head. Therefore, when looking at an object, the eyes must rotate around a vertical axis so that the projection of the image is in the centre of the retina in both eyes. Vergence refers to the simultaneous movement of both eyes in opposite directions to obtain single binocular vision. Convergence is the simultaneous inward movement of both eyes toward each other, and divergence the simultaneous outward movement of both eyes. So to look at an object closer the eyes converge, while for an object farther away they diverge. Because of the different viewpoints observed by the left and right eye however, many other points in space do not fall on corresponding retinal locations. Visual binocular disparity defines this difference between the points of projection in the two eyes. The brain uses this binocular disparity to extract depth information from the two-dimensional retinal images. For this reason eye vergence is considered as an important visual cue for depth perception.

Methods for measuring attention and/or other more or less related cognitive behaviours are known in the prior art. Most of them try to identify and measure many different eye behaviours (e.g. saccades, blinks, eyelid, gaze fixation, pupil dilation, divergence, etc.) to obtain conclusions about attention. A drawback of this type of methods may be that they usually comprise collecting big amounts of data and performing heavy calculations on said collected data, which may cause some inefficiency and, thus, may require powerful and expensive computing resources.

Another inconvenient may be that these methods do not produce clean indicators of attention, since they take into account many different eye behaviours, which may produce measurements mixing attention with other cognitive processes different from attention (such as e.g. perception, memory, experience, etc.)

A further drawback may be that these methods may take too long to obtain more or less reliable conclusions, since they usually measure states (e.g. attention related states) considering long time scales, which may be of several minutes. These long time scales may be necessary for these methods as a consequence of that they consider different eye behaviours, some of which may introduce some disparities in the collected data. It seems to make sense to understand that collecting very big amounts of data and performing complex calculations on said data may be aimed at attenuating/compensating in some way such disparities.

For example, US2007291232A1 discloses a method of the type explained before. This method is aimed at determining mental proficiency level by monitoring point of gaze, pupillary movement, pupillary response, and other parameters in a subject performing a task, collecting the data in a database, analysing the data in the database, and assigning the subject to a score indicating the subject's particular mental proficiency level in real time. Mental proficiency may comprise the ability of paying visual attention when carrying out determined tasks. Thus, it may be understood that an object of this method is to measure attention as a parameter of the mental proficiency. This method has the previously mentioned drawbacks.

SUMMARY OF THE INVENTION

There thus still exists a need for new methods, computer programs and systems of measuring attention of a person that resolve at least some of the above mentioned problems. It is an object of the present invention to fulfil such a need.

In a first aspect, the present invention provides a method of measuring attention of a person comprising presenting one or more stimulus aimed at attracting attention of the person; and obtaining positions of the eyes of the person. The method further comprises detecting one or more eye fixations from the obtained positions of the eyes; and measuring the angle of convergence of the eyes over time from the obtained positions of the eyes during one or more of the detected eye fixations.

A convergence movement (due to the attention paid by the person) will normally be followed by a divergence movement (returning the eyes to their "normal" position once attention has been paid). Such a divergence movement may be seen as a loss of convergence or a negative convergence, whereas such a convergence movement may be seen as a gain of convergence or a positive convergence. Hereinafter, for reasons of simplicity, only the term "convergence" (neither vergence nor divergence) will be used to indicate said two types of movements. In this sense, a positive convergence movement may be defined as a movement during which the angle of convergence increases, and a negative convergence movement may be defined as a movement during which the angle of convergence decreases.

Attention can be associated with unconscious or conscious vision. For instance, attended stimuli are better/earlier consciously seen than non-attended items. Convergence may relate to attention associated with either conscious or unconscious vision. If modulation in convergence occurs, stimuli can be considered consciously attended. In contrast, when no modulation in convergence occurs, stimuli may be considered non-attended or unconsciously attended.

The proposed method, which is based on measuring convergence during fixations, permits measuring attention associated with both types of vision unconscious and conscious.

In the proposed method, convergence measured at the gaze fixation location does not necessary reveal attention to the actual fixated/gazed region of the corresponding stimulus, but the measured convergence may reveal attention to another region.

Convergence modulation occurs at the same time or before the attention shifts, and before the corresponding stimulus is consciously or unconsciously seen. This temporal difference makes the convergence modulation to have a predictive power. It can foretell whether a stimulus will be attended or seen.

Diverse experiments related to the present invention allowed to find a clear relation between eye convergence and attention. It was concluded that during eye fixation the angle of convergence is modulated as a function of the ability to capture attention. Convergence angle seems to be larger after visual stimulation, and this enhancement seems to correlate with bottom-up and top-down attention. The start of the modulation in eye convergence seems to be locked to the onset of the stimulus, while the size of the angle of eye convergence seems to depend on the attentional load that the stimulus receives or attracts.

These results were obtained by testing subjects in a cue/no-cue paradigm. During the task the angle of eye convergence was measured. Surprisingly, the size of the angle of eye convergence was not constant, but was affected by visual stimulation. Once a visual stimulus had been presented (i.e. presentation of stimulus and/or presentation of cue/no-cue stimulus), the angle of eye convergence transiently increased. This increase in the angle of eye convergence was a function of stimulus contrast. It was most pronounced when the stimulus contrast was strongest and gradually decreased for lower contrast levels. For stimuli below a detection threshold, the size of the angle of eye convergence did not change. The size of the angle of eye convergence for detected targets was stronger than for undetected targets. It was found that the modulation of the angle of eye convergence was significantly greater after cue onset.

The observed effects do not reflect the nature of eye convergence (i.e. horizontal eye movements) and depends on the subject's engagement in the task. Control experiments exclude changes in pupil size or the occurrence of micro-saccades as a possible explanation for the observed changes in the angle of eye convergence. Similar effects in the angle of eye convergence were observed when an auditory cue shifts visuospatial attention in congruent and incongruent trials. According to the obtained observations there is a link between small convergence movements during eyes fixation and shifts of visual attention on a 2D (two-dimensional) image without depth clues.

The proposed method, which attributes an innovative role to convergence of eyes, has the advantage of using only one type of eye behaviour (convergence) to conclude about how attentive may be a person. In particular, this method only takes into account the position of the eyes within eye fixations to measure eye convergence as an indicator of attention. Therefore, the necessary data and calculations are drastically reduced in comparison with the prior art methods. Moreover, according to the performed experiments, eye convergence may be considered a reliable indicator of attention isolated from other "disturbing" cognitive processes. In conclusion, the present invention permits measuring attention in a more efficient and clean manner in a very short time. Few seconds of collected data may suffice to evaluate attention.

An advantage of this method is that once positions of the eyes of the person have been obtained during the presentation of the one or more stimulus, the presence of the person is no more required. Then, the obtained positions of the eyes over time are used to perform calculations for detecting eye fixations and measuring the angle of convergence. Thus, in this context, the term "detecting" refers to perform the corresponding calculations on the collected data (positions of the eyes over time) to detect, in this case, eye fixations. Similarly, the term "measuring" refers to perform the corresponding calculations to obtain the angle of convergence over time and related attention measurements.

The method of the invention may be of application to different fields, such as web usability, advertising, sponsorship, package design, automotive engineering, etc. Examples of target stimuli may include websites, television programs, sporting events, films, commercials, magazines, newspapers, packages, shelf displays, consumer systems, software, etc. The resulting data can be statistically analysed and graphically rendered to provide evidence of specific visual patterns. By examining eye convergence the effectiveness of a given medium or product can be determined.

When a person looks at an image, he/she scans the image by making fast saccadic eye movements to particular regions in the scene and fixates for a brief period during which the visual information is perceived. However, not all fixations are perceived consciously or influence behaviour, and some are better observed than others. The present invention permits separating this difference between eyes fixation and perception.

While looking at an image (advertisement, webpage), the regions where the subject looked at may be retrieved and the eye convergence during these fixation periods may be calculated and measured. Regions of interest that show large fluctuations in eye convergence may be indicative of strongly attended regions and of better perceived regions, whereas regions where eye convergence shows less fluctuations are indicative of less attended or perceived regions, despite these regions have been fixated. Fluctuations in convergence may be calculated according to the characteristics of the modulation, i.e. amplitude, velocity, onset latency, duration, etc.

Therefore, the method of the invention may be very useful for e.g. designing advertisements. For example, the method may be performed taking into account different profiles of people watching a product to be advertised. The method may provide data about the parts of the product that e.g. have been more attended by people, in such a way that conclusions about which parts and how salient they may be showed to attract maximum attention can be obtained.

Another application may be to reveal difference in perceptual style, which describes how individuals perceive and understand information. The present invention permits distinguishing between analytical and more irrational people. It may be observed that context-independent observers which are more analytical people have a stronger modulation in eye convergence than context-dependent observers, which are more irrational people. Analytical skills are important for many high demand jobs in a variety of fields and analytical people enjoy using data and facts to reach a conclusion. Certain types of jobs require analytical individuals, like budget analyst, computer systems analyst, market researcher operations, and research analyst. To select among candidates for a job, they may perform e.g. a cue/no-cue task while recording the eye movements. After testing the eye data may be analysed and convergence may be calculated. Candidates with high convergence modulation may be considered likely better analytical persons, and thus better suited for determined jobs.

When performing repetitive tasks it is easy to become bored and overlook important details. Many activities are repetitive especially in assembly work or when visually monitoring products or images. The method of the invention may be very useful to know when a task becomes boring and, thus, it may lead to mistakes. During many repetitive tasks, the eye position can be recorded and eye convergence can be measured. Frequency of convergence may be then calculated during the initial start of the activity. This value may be used as a base line level. Then, during the task, eye convergence may be monitored and compared with the initial frequency of convergence modulation. The modulation in eye convergence reflects the shift in attention. Higher frequency signifies frequent shifts of attention. If a person becomes bored, attention is shifted less times, although the eyes still may move. If the frequency in modulation of convergence drops below a certain threshold, then this may be indicative of less attentive state of the person, who may need to take a break or to be replaced.

Browsing in the Internet or digital media people may be subjected to many advertisements and other types of stimulus. Many of them are however never noticed by the user. The present invention may be used to improve visibility of advertisements or other stimulus of similar type. When browsing or reading text, the eye movements can be recorded e.g. via a suitable webcam (acting as an eye tracker) and eye convergence may be calculated. When eye convergence starts to increase, attention state is increased. This measure can be used to time at the moment of the presentation or alteration of an advertisement. It is more likely that the user notices the appearing stimulus when eye convergence is stronger. Thus the effectiveness of publicity can be improved by monitoring eye convergence.

In a second aspect of the present invention, it is provided a computer program product comprising program instructions for causing a computer to perform a method substantially as hereinbefore described (first aspect of the invention). The invention also relates to such a computer program product embodied on a storage medium (for example, a CD-ROM, a DVD, a USB drive, on a computer memory or on a read-only memory) or carried on a carrier signal (for example, on an electrical or optical carrier signal).

In a third aspect of the invention, a system is provided for measuring attention of a person. This system comprises an eye position tracker; a device for presenting stimulus; and a computing system. This computing system comprises a processor and a memory, the memory storing computer executable instructions that, when executed, cause the computing system to perform a method substantially as hereinbefore described (first aspect of the invention).

Additional objects, advantages and features of embodiments of the invention will become apparent to those skilled in the art upon examination of the description, or may be learned by practice of the invention.

BRIEF DESCRIPTION OF THE DRAWINGS

Particular embodiments of the present invention will be described in the following by way of non-limiting examples, with reference to the appended drawings, in which.

DETAILED DESCRIPTION OF EMBODIMENTS OF THE INVENTION

In the following description, numerous specific details are set forth in order to provide a thorough understanding of the present invention. It will be understood by one skilled in the art however, that the present invention may be practiced without some or all of these specific details. In other instances, well known elements have not been described in detail in order not to unnecessarily obscure the description of the present invention.

Figure 7:
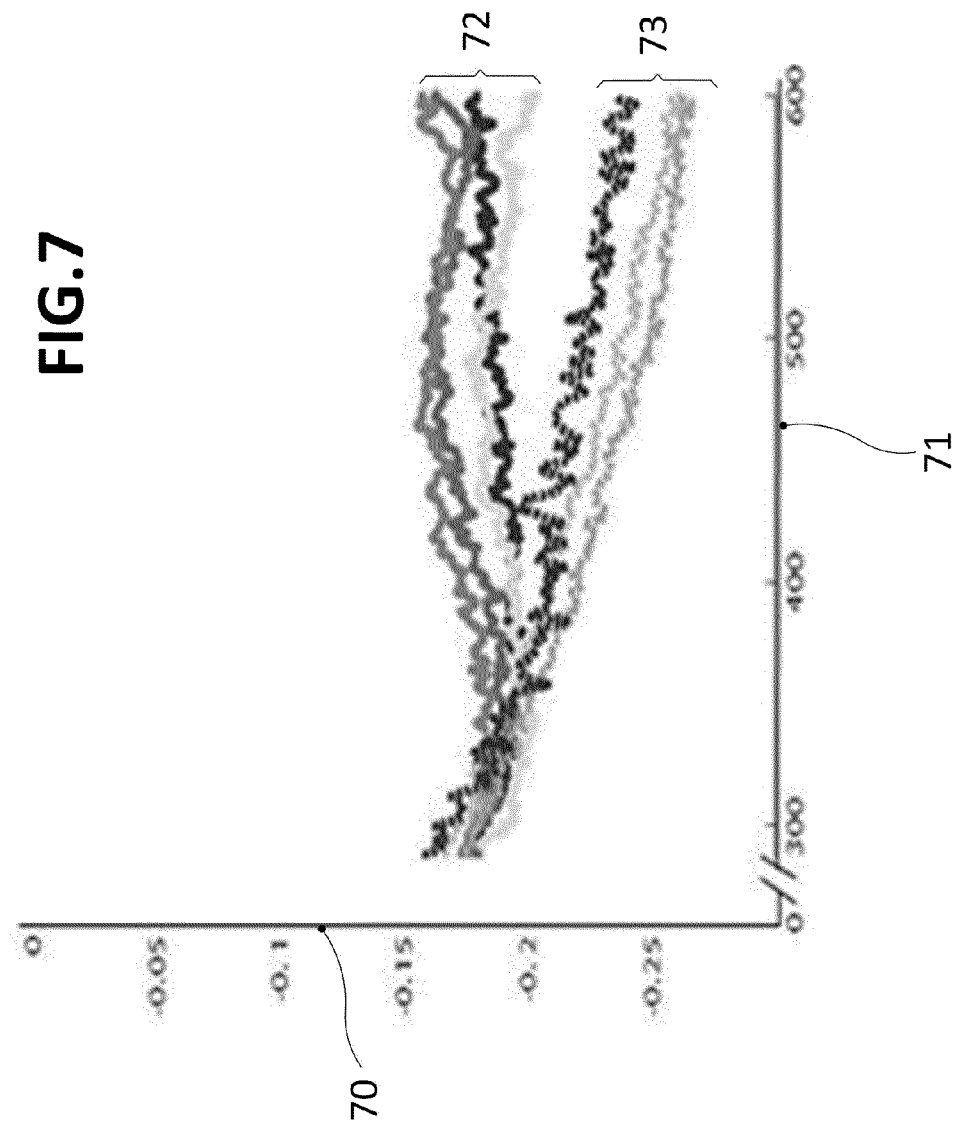
FIG. 7 graphically illustrates that attention associated with conscious vision may normally have a convergence modulation greater than the attention associated with unconscious vision.

FIG. 7 graphically illustrates that attention associated with conscious vision 72 may normally have a convergence modulation 70 greater than the attention associated with unconscious vision 73. The vertical axis 70 of the graphic shown refers to angle of convergence, whereas the horizontal axis 71 refers to time. This graphic shows that (consciously) seen stimuli cause higher modulation of convergence 72, and that not seen stimuli cause lower modulation of convergence 73. Hence, the proposed method of measuring attention (based on measuring convergence) may also aid to differentiate between attention associated with seen and not seen stimuli.

Figure 1B:
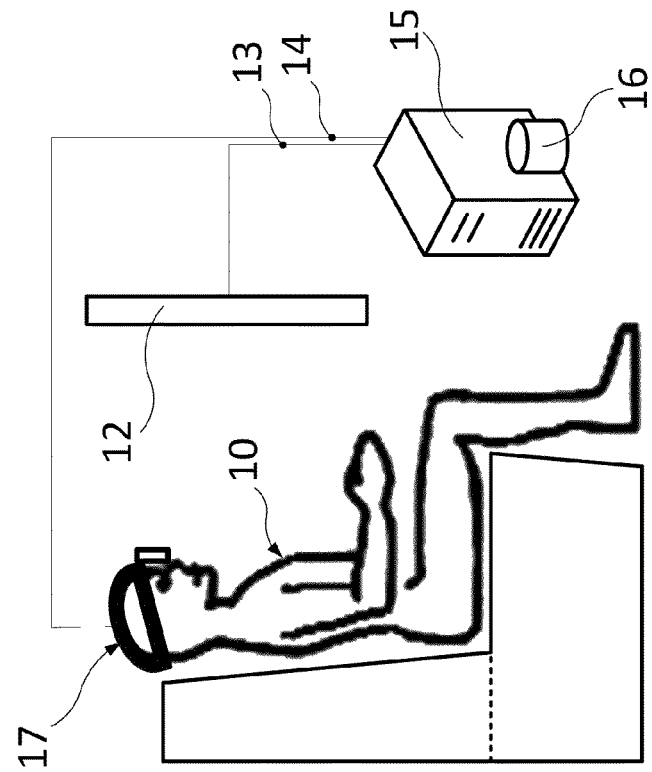
FIGS. 1a and 1b show schematic representations of a first and a second system for measuring attention, according to embodiments of the invention.
Figure 1A:
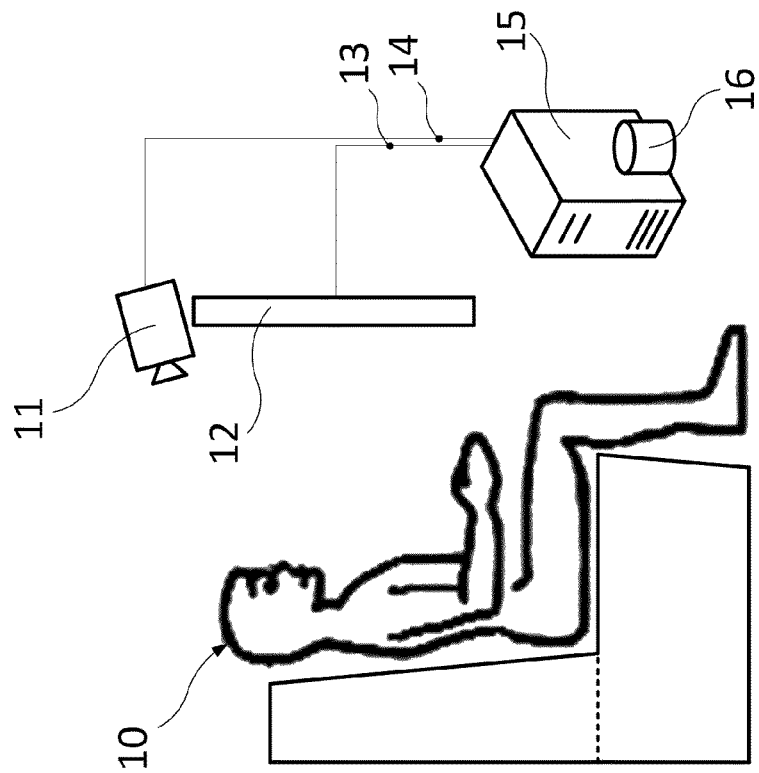

FIG. 1a illustrates a system for measuring attention of a person 10. This system may comprise a device for presenting stimulus (such as e.g. a screen 12), an eye position tracker (such as e.g. a suitable camera 11), and a computing system 15 configured to execute a computer program configured to perform embodiments of a method for measuring attention. The computer 15 may comprise a repository (such as a conventional hard disk 16) to store and retrieve data required by said computer program.

The camera 11 may be positioned in such a way that positions of the eyes of the person 10 may be properly obtained to detect fixations of the eyes and to calculate data related to the angle of convergence of the eyes. Both the camera 11 and the screen 12 may be suitably connected 13, 14 with the computer 15, such that the computer 15 may interchange suitable signals with the screen 12 mainly to present the corresponding visual stimulus, and may interchange suitable signals with the camera 11 mainly to obtain positions of the eyes. Said connections 13, 14 may be wired and/or wireless connections.

The system of FIG. 1*a* may comprise proper means to hold the head of the person 10 in a substantially fixed position. These fixation means are not shown in the figure. Alternatively, the system may not comprise such means, in which case the camera 11 may comprise a suitable software (or computer program) to evaluate the movements of the head of the person 10. Since movements of the head may distort in some way the captured movements of the eyes, this software may take into account the movements of the head to attenuate said potential distorts. This camera 11, thus, will be able to send "clean" positions of the eyes to the computer 15. Alternatively, the camera 11 may not comprise such software, in which case an equivalent computer program may be comprised in the computer 15. In this case, the camera 11 will only send to the computer 15 signals representing captured images of the head (including, of course, the eyes) and the computer 15 will attenuate potential distorts due to movements of the head.

FIG. 1*b* illustrates another system for measuring attention of the person 10 very similar to the system of FIG. 1*a*. The only difference between them is that the system of FIG. 1*b* comprises an eye tracker 17 which is different from the eye tracker 11 of FIG. 1*a*. In this case, a software for compensating movements of the head will be not necessary because the eye tracker 17 moves jointly with the head.

Alternatively to a camera 11 and to a head-mounted tracker 17, embodiments of the system may comprise a device suitable for performing Electrooculographies (EOGs). And, alternatively, embodiments of the system may comprise scleral coils.

In general, eye trackers necessarily measure the rotation of the eyes with respect to the measuring system. If the measuring system is head mounted, as the device 17 of FIG. 1*b*, eye-in-head angles are measured. If the measuring system is table mounted, as the camera 11 of FIG. 1*a*, then gaze angles are measured.

The most widely used current designs are video-based eye trackers. A camera focuses on one or both eyes and records their movement as the viewer looks at some kind of stimulus. Most modern eye-trackers use contrast to locate the centre of the pupil and use infrared and near-infrared non-collimated light to create a corneal reflection. The vector between these two features can be used to compute gaze intersection with a surface after a simple calibration for an individual.

Light, typically infrared, is reflected from the eye and sensed by a video camera or some other specially designed optical sensor. The information is then analysed to extract eye rotation from changes in reflections. Video based eye trackers typically use the corneal reflection and the centre of the pupil as features to track over time. A more sensitive type of eye tracker uses reflections from the front of the cornea and the back of the lens as features to track. A still more sensitive method of tracking is to image features from inside the eye, such as the retinal blood vessels, and follow these features as the eye rotates.

The systems of FIGS. 1*a* and 1*b* may be suitable for performing a method comprising presenting on the screen 12 one or more stimulus (images) aimed at attracting attention of the person, and obtaining from the eye tracker 11 or 17 positions of the eyes of the person. Once the images presented and the positions of the eyes obtained, the method may comprise detecting the time intervals in which fixations of the eyes have occurred from the obtained eye positions. Then, within each of said eye fixations, the angle of convergence of the eyes and its variation over time may be calculated. Finally, some indicators or measurements of attention may be derived from said calculated angle of convergence.

The angle of convergence may be calculated from the obtained positions of the eyes by applying any suitable known algorithm aimed at that. Said algorithms, which are mainly based on trigonometric calculations, are well known, so no particular details about them will be provided herein.

In some embodiments, the method may comprise presenting a plurality of stimulus (images) in sequence until a predefined condition is achieved. More particularly, the method may comprise presenting one or more pairs of related stimulus (images), each of said pairs of related stimulus comprising a first stimulus and a second stimulus, the second stimulus comprising an alteration of the first stimulus. And more particularly, the method may comprise presenting at least one cue between the presentation of the first stimulus and the presentation of the second stimulus, said cue providing a hint of what is the alteration of the second stimulus with respect to the first stimulus.

The predefined condition may be considered as achieved when a predefined time is reached. Alternatively to this, the predefined condition may be considered as achieved when a predefined number of presented stimulus is reached.

The objective of the cue is to shift attention or induce attention. When convergence is modulated, it may be assumed that the cue works. Thus, the effectiveness or success of a cue can be tested. The cue may comprise one or more visual signals, and/or one or more auditory signals, and/or more tactile signals, etc. Any of these different types of signals may be combined in a same cue in such a way that the cue may be useful to evaluate how different sensory experiences may cause more or less attention in front of e.g. a particular image, pair of related images, sequence of images, sequence of pairs of related images, and so on.

A visual signal may point to a particular region or object of the corresponding stimulus. Examples of cues only comprising visual signals will be explained in reference to FIGS. 2 and 3.

Example of cues comprising auditory signals may be, for instance, a voice saying "look at the wheels of the car" or "look, the wheels are nice". A reaction to said first auditory cue may be e.g. the eyes having fixated the wheels but the convergence does not having modulated, in which case it may be assumed that this cue does not work. However, a reaction to the second auditory cue may be e.g. the eyes having fixated the wheels and, moreover, the convergence having modulated, in which case it may be assumed that this cue works.

An example of tactile cue may be e.g. a specific device pressing a particular point of a hand in such a way that said particular point provides a hint of where is the alteration of the second stimulus with respect to the first stimulus.

In multimedia environments, particularly in videogames, it may be very suitable the use cues combining visual and/or auditory and/or tactile signals. For instance, if it is an objective to highly attract attention of the player, a cue combining an impacting image, an impacting sound and an impacting vibration of a joystick may be used. Embodiments of the system and method of the invention may be very suitable thus to design e.g. videogames; in particular, said embodiments may be very suitable to evaluate the impact on the player's attention of, and thus accurately design, determined virtual situations or events (stimulus with cues in the context of the present invention) in a videogame.

Figure 2:
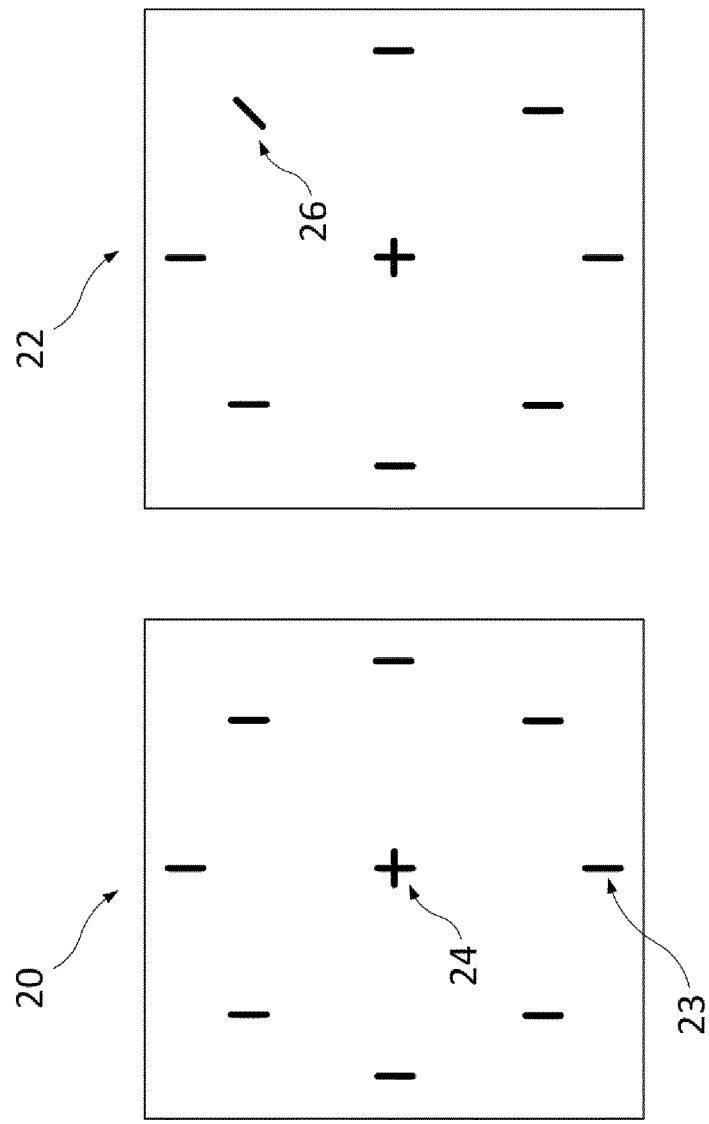
FIG. 2 illustrates a first set of stimulus to be presented in sequence, according to an embodiment of the invention.

FIG. 2 illustrates a pair of visual stimulus (or images), in which a first stimulus 20 is firstly presented, and a second stimulus 22 is secondly presented. Time between said presentations may vary depending on the circumstances and objectives of each test. The first stimulus 20 may comprise a cross 24 in the centre of the image and several vertical lines 23 around the cross 24. The second stimulus 22 may comprise an alteration with respect to the first stimulus 20. This alteration may be the inclination 26 of one of the vertical lines surrounding the cross 24. The angle of inclination may vary e.g. from one trial to another.

The pair of stimulus of FIG. 2 is aimed at testing bottom-up attention where the saliency or contrast (inclined line 26) of the stimulus 22 can be very or slightly different than the previously presented stimulus 20. This test permits evaluating the ability of the observer to automatically and/or involuntarily attend to the variation 26. When convergence angle increases then stimulus is effective in attracting attention and is more likely to be seen by the observer. This test can be used to see how well people can ignore (i.e. get not distracted by) the variation 26.

Figure 3:
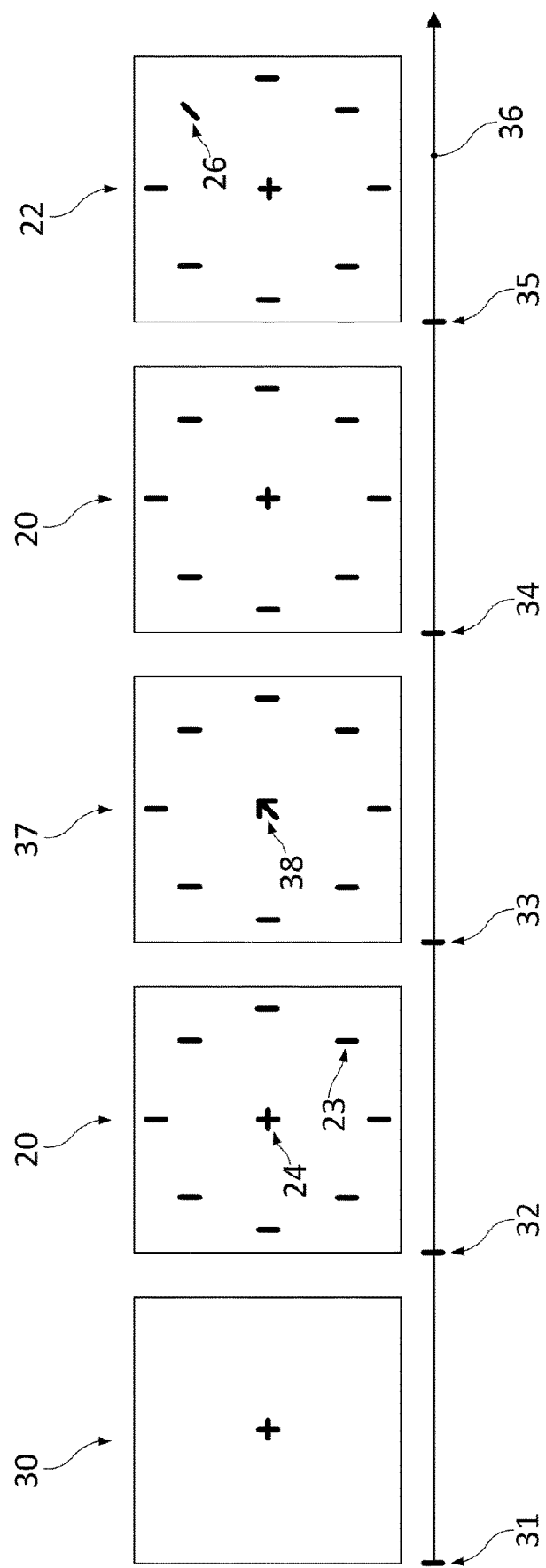
FIG. 3 illustrates a second set of stimulus to be presented in sequence, according to another embodiment of the invention.

FIG. 3 illustrates the same pair of visual stimulus 20, 22 of FIG. 2, but with further presentations of stimulus/cues. This figure also shows a time scale 36 according which presentations of stimulus/cues are performed at different points of said scale 36. In this case, a stimulus 30 previous to the first stimulus 20 (from FIG. 2) is presented at an initial time 31. After that, the stimulus 20 (from FIG. 2) is presented at a time 32, which may be e.g. 300 ms after the initial time 31. Next, a cue 37 is presented at a time 33, which may be e.g. 1300 ms after the initial time 31. Afterwards, the stimulus 20 (from FIG. 2) is again presented at a time 34, which may be e.g. 1400 ms after the initial time 31. Finally, the stimulus 22 (from FIG. 2) is presented at a time 35, which may be e.g. 2400 ms after the initial time 31. The cue 37 may comprise e.g. an arrow 38 pointing to a vertical line which will be presented inclined 26 in the final stimulus 22.

The sequence of stimulus/cues of FIG. 3 is aimed at testing top-down attention where the observer is instructed to move its attention, before presenting the final stimulus 22, to the line which will be shown inclined 26 in said final stimulus 22. The cue 37 improves performance of the detection of the variation 26. Thus, the effectiveness of the cue 37 can be tested. If the cue 37 evokes little change in convergence then the cue 37 may be considered little effective. Since bottom-up attention and top-down attention are processes performed by different brain regions, the sequences of FIGS. 2 and 3 may be suitable to probe different cognitive mechanisms related to attention.

Alternatively to presenting pairs of related stimulus, the method may comprise presenting unrelated stimulus and without cues for free viewing on the part of the person to be evaluated. This way of presenting stimulus may be of application to e.g. design of advertisements, in which case the method of the invention may help to conclude which parts and how salient they should be presented in order to achieve particular effects in the attention of people.

In embodiments of the invention, the method may further comprise obtaining, for one or more of the presented stimulus, at least one voluntary action from the person in response to the presented stimulus. And particularly, in embodiments presenting one or more pairs of related stimulus, the method may comprise obtaining, for one or more of the second stimulus (of the pairs of stimulus), a voluntary action from the person in response to the second stimulus.

This voluntary action from the person may be e.g. a click of mouse indicating something about one of the presented stimulus. If said stimulus is a second stimulus of a pair of related stimulus, the click of mouse may refer to which is the alteration of the second stimulus with respect to the first stimulus perceived by the person. This voluntary action may be useful to know what the visual system of the person has selected unconsciously or consciously. The convergence will indicate whether the stimulus has been attended or perceived. Thus fixation is to know what is seen and convergence is to know what is attended.

Figure 4:
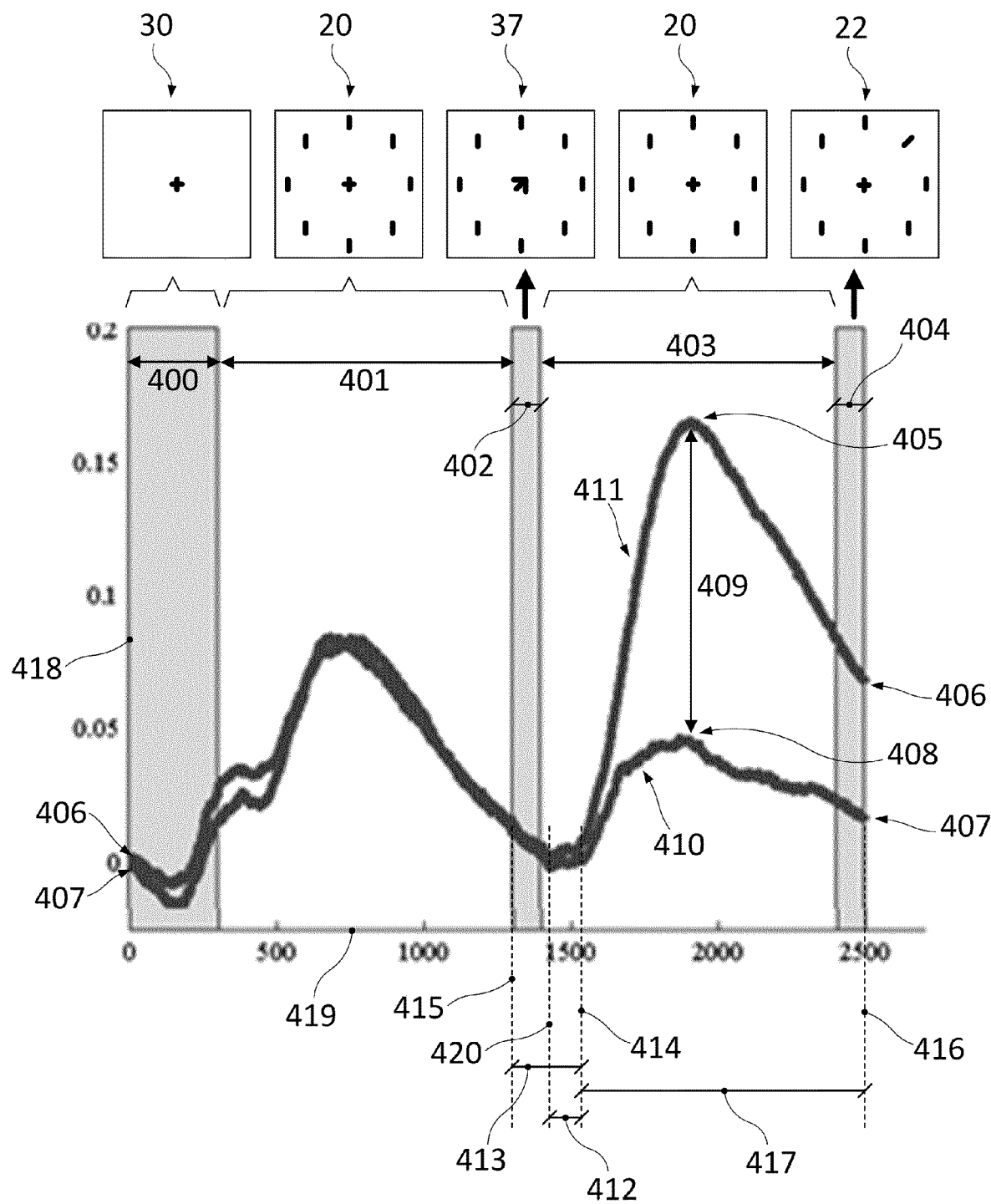
FIG. 4 illustrates collected data related to eye convergence, according to embodiments of the invention.

FIG. 4 illustrates a representation of collected data related to eye convergence, according to embodiments of the invention. In particular, this figure shows how the angle of convergence 418 may behave over time 419 according to a first set of collected data 407 and to a second set of collected data 406. Said collected positions of the eyes 406, 407 may correspond to different experiments according to the sequence of stimulus/cues shown in FIG. 3. FIG. 4 also reflects that a few seconds of collected data 406, 407 may suffice to obtain conclusions about attention. In this case, only 2.5 seconds (2.500 milliseconds) of collected eye positions are represented in FIG. 4.

FIG. 4 refers to a particular sequence of stimulus/cues, but said sequence may be just a sub-sequence of a more or less larger sequence of stimulus and cues. In this sense, the graphic shown may be just a sub-graphic (or a part) of a more or less larger graphic representing the overall data collected during said larger sequence of stimulus and cues. Only this "small" graphic is shown in FIG. 4 for reasons of simplicity, but it is considered enough to understandably provide the descriptions that follow.

In embodiments of the method, measuring the angle of convergence of the eyes comprises measuring the speed at which the angle of convergence substantially changes. A higher speed 411 may be e.g. assumed as an indicator of higher attention or of having the ability of quickly attending. A lower speed 410 may be e.g. assumed as an indicator of lower attention or of having the defect of slowly attending. Different levels between a highest speed and a lowest speed may be used e.g. to classify different people about the ability of quickly or slowly attending.

In some embodiments, measuring the angle of convergence of the eyes may comprise measuring the time during which the angle of convergence remains substantially unchanged. It may be assumed e.g. that the angle of convergence remains substantially unchanged when the angle of convergence is between a higher and a lower threshold over time. FIG. 4 shows an example of time interval 412 in which the angle of convergence remains substantially unchanged. For example, very long intervals of time with a substantially constant angle of eye convergence may be assumed as a poor ability of paying attention, whereas, very short intervals of time with a substantially constant angle of eye convergence may be assumed as a good ability of paying attention. These and intermediate levels may be used to classify different people about the ability of paying poor or good attention.

In embodiments of the method, measuring the angle of convergence of the eyes comprises measuring, for one or more of the eye fixations 414 to 416, the time 412 substantially elapsed from when the eye fixation substantially starts 420 to when the angle of convergence substantially starts to increase 414 within said eye fixation 414 to 416. A long time between start of the fixation and start of convergence may indicate that the person may not be able to quickly pay attention to something that has been seen. Different levels of time between start of fixation and start of convergence may be used to classify different people about the ability of quickly or slowly attending to something that has been seen.

Embodiments of the method may further comprise: determining, for one or more of the eye fixations 414 to 416, the stimulus 37 whose presentation has theoretically caused the eye fixation 414 to 416; and measuring, for one or more of the determined stimulus 37, the time 413 substantially elapsed from when the stimulus is substantially presented 415 to when the angle of convergence substantially starts to increase 414 within the eye fixation 414 to 416 caused by the determined stimulus 37. If the stimulus has probed effectiveness, long times between presentation 415 of the stimulus 37 and start of convergence 414 may indicate attentional problems of the person. If the person is catalogued as attentionally normal, long times between presentation of the stimulus and start of convergence may indicate ineffectiveness of the stimulus. Different levels of time between presentation of the stimulus and start of convergence may be defined to categorize attentional profile of people and/or effectiveness of stimulus.

In some embodiments, measuring the angle of convergence of the eyes may comprise measuring, for one or more of the eye fixations 414 to 416, the time 417 substantially elapsed from when the angle of convergence substantially starts to increase 414 to when the angle of convergence substantially ends to decrease 416 within the eye fixation 414 to 416. A long time between start of convergence increase and end of convergence decrease may indicate e.g. a good ability of the person for maintaining attention. Different levels of time between start of convergence increase and end of convergence decrease may be defined to classify people about the ability of maintaining attention.

In embodiments of the method, measuring the angle of convergence of the eyes may comprise obtaining, for one or more of the eye fixations 414 to 416, the maximum angle of convergence 405 from when the eye fixation substantially starts 420 to when the eye fixation substantially ends. And more particularly, measuring the angle of convergence of the eyes may comprise obtaining the difference 409 of the maximum 405 angle of convergence with respect to the maximum 408 of a previously obtained baseline 407.

This previously obtained baseline may correspond to the one obtained from the second set of collected data 406, which may have been previously obtained by means of previous executions of the method or previous sub-sequences of stimulus/cues within the same execution. Said previous executions of the method and/or previous sub-sequences within the same execution may have been applied to the same person. Alternatively, the previous executions of the method may be previous executions applied to other persons according to e.g. a determined person profile.

Comparison of a first set of collected data 407 (or previously obtained baseline) and a second set of collected data 406 may be very useful in e.g. medical applications. For instance, effectiveness of medicines which are supposed to improve attention may be tested by applying said principle. In this case, the second set of collected data 406 may have been obtained from a person that has taken the medicine, whereas the first set of collected data 407 may have been taken from the same person without having taken the medicine. A significant difference 409 of the maximum 405 angle of convergence of the second set of collected data 406 with respect to the maximum 408 of the first set of collected data 407 (previously obtained baseline 407), may indicate a significant improvement of attention, in which case a good effectiveness of the medicine may be assumed.

Other parameters may be considered when comparing the first set of collected data 407 (or previously obtained baseline) and the second set of collected data 406, such as for example: speed at which the angle of convergence substantially changes, time during which the angle of convergence remains substantially unchanged, time substantially elapsed from when the eye fixation substantially starts to when the angle of convergence substantially starts to increase within said eye fixation, time substantially elapsed from when the stimulus is substantially presented to when the angle of convergence substantially starts to increase, time substantially elapsed from when the angle of convergence substantially starts to increase to when the angle of convergence substantially ends.

In some embodiments, the method may further comprise e.g. obtaining and providing a graphic of the type described in reference to FIG. 4 from the result of measuring the angle of convergence. Alternatively, the method may further comprise obtaining and providing a predefined value indicating the level of attention from an array which correlates attention and angle of convergence (i.e. the result of measuring the angle of convergence). Alternatively, the method may further comprise applying a formula which provides a level of attention depending on the measured angle of attention (i.e. the result of measuring the angle of convergence). And alternatively, the method may further comprise obtaining and providing any combination of these information elements: a graphic of the type described in reference to FIG. 4, a level of attention from an array correlating attention and angle of convergence, a level of attention by applying a suitable formula.

The array may be customizable in such a way that e.g. different scales of attention values and/or of convergence angle values may be adapted to the particular circumstances in which the method is used. Similarly, the formula may also be customizable in such a way that e.g. different factors and/or summands and/or other operands may be defined for their application to the obtained angle of convergence, in such a way that the formula may be adapted to the specific circumstances under which the method is used.

In the embodiments where different parameters related to the angle of convergence are considered, the above mentioned array may be a multidimensional array in which each dimension may represent one of said parameters. Examples of parameters related to the angle of convergence may be e.g. the angle of convergence itself, the speed at which the angle of convergence substantially changes, the time during which the angle of convergence remains substantially unchanged, etc. A scale comprising different levels for each of said parameters may be defined, such that the values calculated for each of the parameters may be correlated with said different levels of the related scale. For instance, in some applications, a scale related to the speed of change of the angle of convergence may comprise e.g. 10 levels, wherein the level SL-0 corresponds to a minimum speed, the level SL-10 corresponds to a maximum speed, and the levels from SL-1 to SL-9 are intermediate levels corresponding to intermediate speeds between the levels SL-0 and SL-10.

For example, in this type of multidimensional array, a first dimension may represent the scale of levels related to the angle of convergence, a second dimension may represent the scale of levels related to the speed at which the angle of convergence substantially changes, a third dimension may represent the scale of levels related to the time during which the angle of convergence remains substantially unchanged, and so on. Thus, a particular level of attention may be defined for each combination of levels of different dimensions. For example, a level of attention AL-5 (whose meaning may be e.g. "medium attention") may be attributed to the following combination of dimensional levels: CA-4 (level 4 of the angle of convergence), SL-6 (level 6 of the speed at which the angle of convergence substantially changes), and UL-5 (level 5 of the time during which the angle of convergence remains substantially unchanged). Equivalent principles may be used to correlate the rest of attention levels with the corresponding parameters (angle of convergence, speed, etc.).

Attentional Deficit and Hyperactivity Disorder (ADHD, which includes ADD) and the three related sub-types (ADHD-PI or ADHD-I, ADHD-HI or ADHD-H, and ADHD-C) are one of the more frequent psychopathological disorders in children and adolescents (3-6%). The routine assessment of ADHD (including ADD and related sub-types), which is based on questionnaires and developmental, physical and mental examination, has many flaws and is inaccurate. While clear symptoms are present at 3 years of age, current diagnosis cannot be done before the age of 6 (DSM-IV/DSM-V) prohibiting early treatment, which is essential for preventing personal and social problems, and economical costs associated to ADHD (including ADD and related sub-types).

Problems in binocular vision are common in a number of neural disorders, like ADHD (including ADD and related sub-types). The critical period for the development of binocular vision in humans is between three and eight months of age, with sensitivity to damage extending up to at least three years of age. It is thus important to evaluate children for binocular anomalies at early developmental stages (3 months-2 years) to determine whether they will develop neurological disorders like ADHD (including ADD and related sub-types). Current assessment methods do not allow the diagnosis of ADHD (including ADD and related sub-types) before the age of six.

Embodiments of the proposed method could be used to test, detect, understand and diagnose neurological disorders in humans (including adults, children, infants and newborns) related to ADHD (including ADD and related sub-types).

In particular, a method for measuring ADHD (including ADD and related sub-types) in a person is provided comprising any of the previously described embodiments of the method of measuring attention of a person. An advantage of this method for measuring ADHD (based on measuring eye convergence) may be that signs of ADHD (including ADD and related sub-types) may be detected at an early developmental stage in infants, children but also adults. Early detection may make visual treatment more effective as it can start early on during cortical development, e.g. during the critical period of binocular vision. Problems in binocular vision can be treated by optometrists through vision therapy.

To measure mental disorders, convergence modulation from patient or susceptible person may be compared to convergence modulation from healthy individuals, and/or comparison in convergence modulations may be performed between different conditions. Any of the embodiments of the method for measuring attention described herein may be used to obtain such convergence modulations to be compared.

In general, if convergence modulation is absent or different from convergence modulation in normal subjects, this may be indicative of neurological disorder. Different statistical techniques can be used to measure differences between convergence modulations. Different algorithms, such as probabilistic neural networks, may be used for classification purposes (e.g. control vs. clinical cases). Children may be tested under visual tasks designed for their age.

Figure 5:
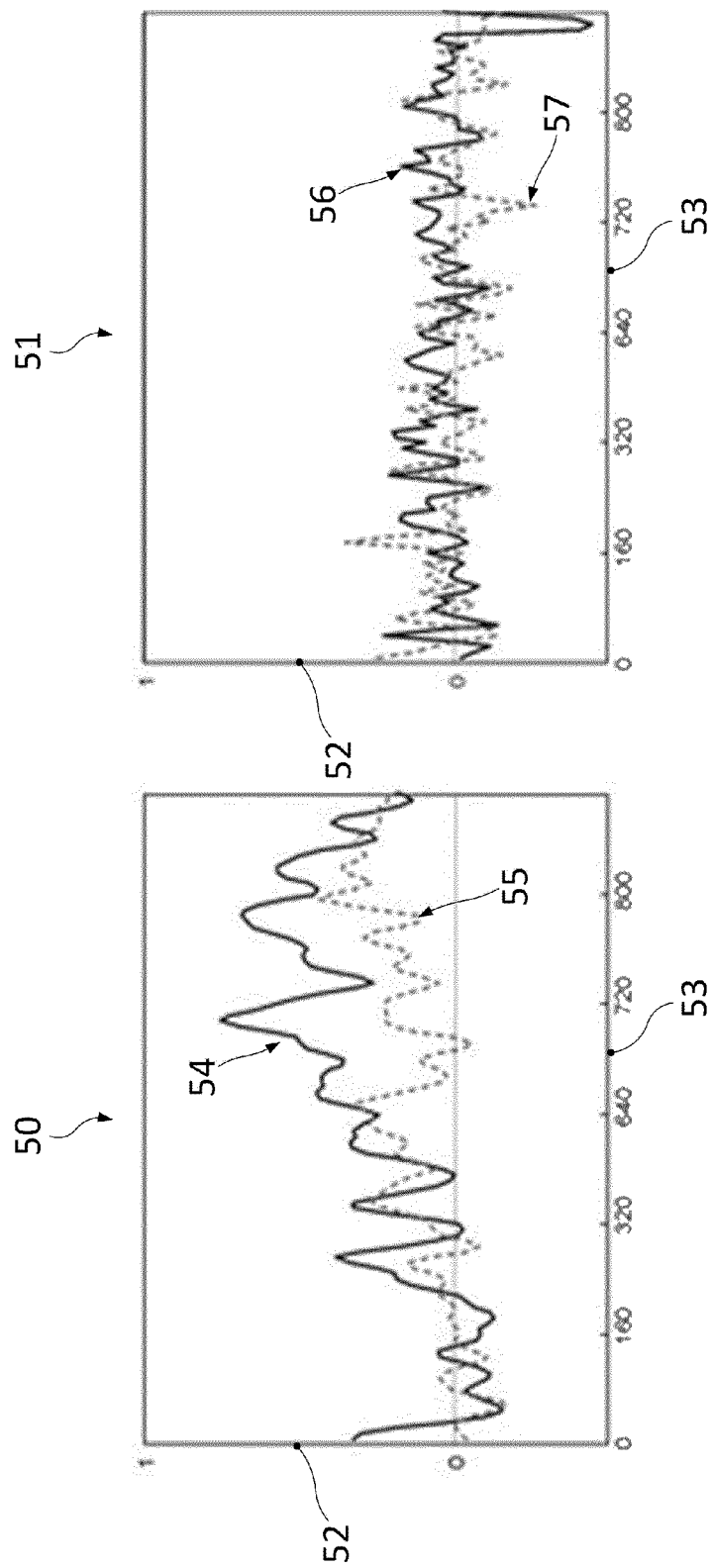
FIG. 5 graphically illustrates collected data about eye convergence related to a normal person and to a person with ADHD, according to embodiments of the invention.

FIG. 5 graphically illustrates collected data about eye convergence related to a normal person and to a person with ADHD, according to embodiments of the invention. In particular, this figure shows a first graphic 50 reflecting modulation in convergence in a normal child (7 years old), and a second graphic 51 reflecting modulation in convergence in a non-medicated child with ADHD (8 years old), in both cases tested in a cue/no-cue task. The horizontal axis 53 refers to time in milliseconds and the vertical axis 52 refers to angle of convergence.

The first graphic 50 shows the evolution of the angle of convergence 52 over time 53 for attended stimulus 54 by the normal person (continuous line), and for non-attended stimulus 55 by the normal person (dashed line). The second graphic 51 shows the evolution of the angle of convergence 52 over time 53 for attended stimulus 56 by the person with ADHD (continuous line), and for non-attended stimulus 57 by the person with ADHD (dashed line).

With respect to the first graphic 50, a significant modulation of the angle of convergence 52 and significant differences between the attended 54 and non-attended 55 conditions are appreciated in the normal person. In relation to the second graphic 51, neither significant modulation of the angle of convergence 52 nor significant differences between the attended 56 and non-attended 57 conditions are appreciated in the person with ADHD.

Figure 6:
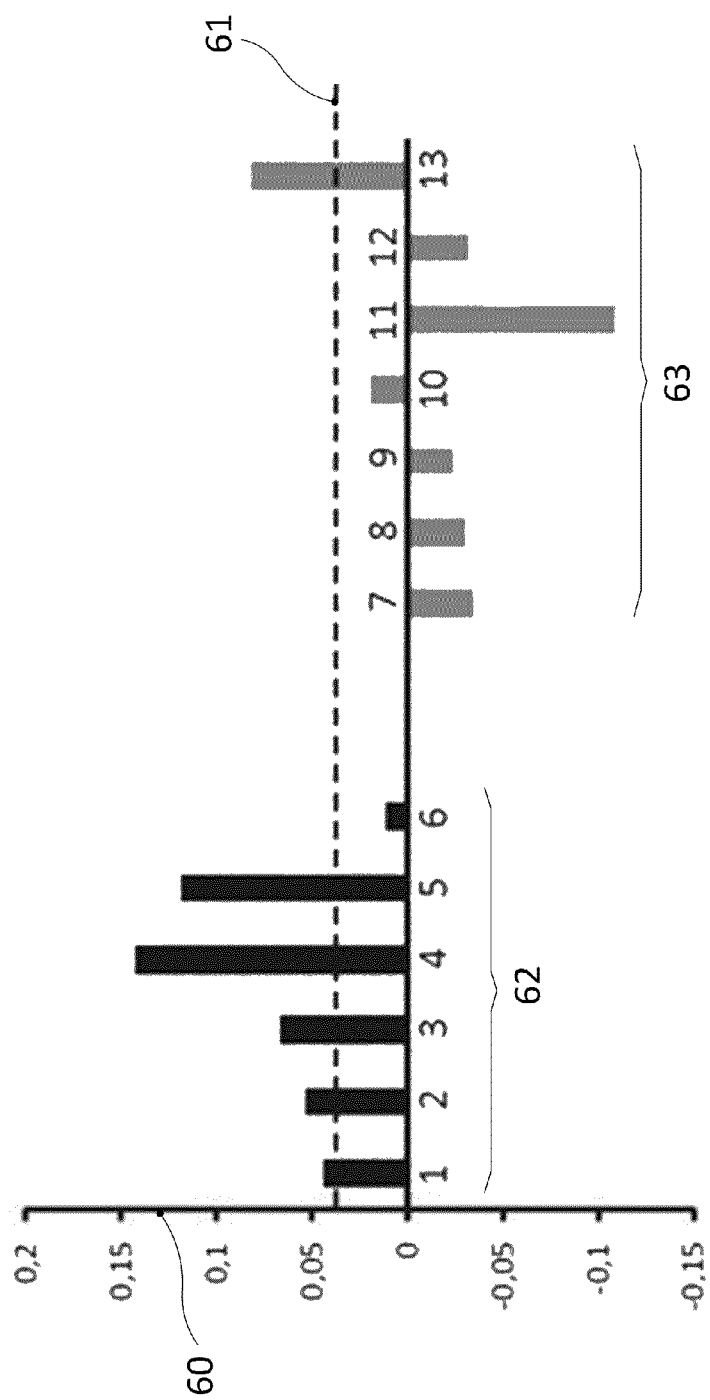
FIG. 6 graphically illustrates data about convergence modulation related to normal people and to people with ADHD, according to embodiments of the invention.

FIG. 6 graphically illustrates data about convergence modulation related to normal people and to people with ADHD, according to embodiments of the invention. In this graphic, whose vertical axis 60 refers to convergence modulation, six normal people 62 and seven people with ADHD 63 are represented. This seven people 63 have been diagnosed with ADHD with the DSM-IV method. The method proposed herein permits concluding that convergence modulation is significantly higher in normal children 62 in comparison with children with ADHD 63. A threshold (dashed line) 61 could be defined to differentiate between healthy people and people with ADHD.

Although only a number of particular embodiments and examples of the invention have been disclosed herein, it will be understood by those skilled in the art that other alternative embodiments and/or uses of the invention and obvious modifications and equivalents thereof are possible. Furthermore, the present invention covers all possible combinations of the particular embodiments described. Thus, the scope of the present invention should not be limited by particular embodiments, but should be determined only by a fair reading of the claims that follow.

Further, although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source code, object code, a code intermediate source and object code such as in partially compiled form, or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means.

When the program is embodied in a signal that may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

The invention claimed is:

1. A method of measuring attention of a person comprising:
    presenting one or more stimuli on a display screen to attract attention of the person;
    obtaining positions of eyes of the person while presenting the one or more stimuli on the display screen, the obtaining performed using an eye position tracker device;
    detecting, by a processor, one or more eye fixations from obtained positions of the eyes, each of the one or more eye fixations being a time period of stable gaze between two saccadic eye movements, the time period from 100 millisecond to 1 second;
    calculating by the processor, from the positions of the eyes obtained during each of the one or more eye fixations, an angle of convergence of the eyes and a variation in the angle of convergence over time within an eye fixation;
    determining a level of attention of the person from an array correlating attention and one or both of the angle of convergence of the eyes and the variation in the angle of convergence over time; and
    presenting one or more additional stimuli on the display screen to attract attention of the person, the one or more additional stimuli having been timed or altered according to the determined level of attention of the person.

2. The method according to claim 1, the presenting one or more stimuli comprises presenting a plurality of stimuli in sequence until a predefined condition is achieved.

3. The method according to claim 2, the plurality of stimuli comprises one or more pairs of related stimuli, each of the pairs of related stimuli comprising a first stimulus and a second stimulus, the second stimulus comprising an alteration of the first stimulus.

4. The method according to claim 3, the presenting the one or more of the pairs of related stimuli comprises presenting at least one cue between the presentation of the first stimulus and the presentation of the second stimulus, the cue providing a hint of what is the alteration of the second stimulus with respect to the first stimulus.

5. The method according to claim 1, further comprising obtaining, for one or more of the presented stimuli, at least one voluntary action from the person in response to the one or more presented stimuli.

6. The method according to claim 3, further comprising obtaining, for one or more of the second stimuli, a voluntary action from the person in response to the second stimulus.

7. The method according to claim 1, wherein the calculating the angle of convergence of the eyes comprises measuring a speed at which the angle of convergence changes.

8. The method according to claim 1, wherein the calculating the angle of convergence of the eyes comprises measuring a time during which the angle of convergence remains unchanged.

9. The method according to claim 1, wherein the calculating the angle of convergence of the eyes comprises measuring, for one or more of the eye fixations, a time elapsed from when the eye fixation starts to when the angle of convergence starts to increase within the eye fixation.

10. The method according to claim 1, wherein the calculating the angle of convergence of the eyes comprises measuring, for one or more of the eye fixations, the time elapsed from when the angle of convergence starts to increase to when the angle of convergence decrease ends within the eye fixation.

11. The method according to claim 1, wherein the calculating the angle of convergence of the eyes comprises obtaining, for one or more of the eye fixations, a maximum angle of convergence from when the eye fixation starts to when the eye fixation ends.

12. The method according to claim 11, wherein the calculating the angle of convergence of the eyes comprises obtaining a difference of the maximum angle of convergence with respect to a previously obtained baseline.

13. The method according to claim 1, further comprising:
    determining, for one or more of the eye fixations, the one or more stimuli that has theoretically caused the eye fixation yielding one or more determined stimuli; and
    measuring, for the one or more determined stimuli, a time elapsed from when the one or more determined stimuli is or are presented to when the angle of convergence starts to increase within the eye fixation caused by the one or more determined stimuli.

14. The method according to claim 2, further comprising obtaining, for one or more of the presented stimuli, at least one voluntary action from the person in response to the presented one or more stimuli.

15. The method according to claim 4, further comprising obtaining, for one or more of the presented stimuli, at least one voluntary action from the person in response to the one or more of the presented stimuli.

16. A non-transitory computer readable medium storing computer-executable instructions configured to cause a computer to perform a method for measuring attention of a person according to claim 1.

17. A method of measuring Attentional Deficit and Hyperactivity Disorder in a person, comprising the method according to claim 1.

18. A non-transitory computer readable medium storing computer-executable instructions configured to cause a computer to perform a method for measuring Attentional Deficit and Hyperactivity Disorder in a person according to claim 17.

19. A system for measuring attention of a person comprising:
    an eye position tracker device;
    a display screen for presenting one or more stimuli;
    a computing system comprising a processor and a memory; the memory configured to store computer executable instructions that, when executed, cause the computing system to perform a method comprising:
        presenting, through the display screen, one or more stimuli aimed to attract attention of the person;
        obtaining, through the eye position tracker device, positions of eyes of the person while the one or more stimuli are presented through the display screen;

detecting one or more eye fixations from obtained positions of the eyes, each of the one or more eye fixations being a time period of stable gaze between two saccadic eye movements, the time period from 100 millisecond to 1 second;

calculating from the positions of the eyes obtained during each of the one or more eye fixations, an angle of convergence of the eyes and a variation in the angle of convergence over time within an eye fixation;

determining a level of attention of the person from an array correlating attention and one or both of the angle of convergence of the eyes and the variation in the angle of convergence over time; and presenting one or more additional stimuli on the display screen to attract attention of the person, the one or more additional stimuli having been timed or altered according to the determined level of attention of the person.

\* \* \* \* \*